(12) United States Patent
Ahn et al.

(10) Patent No.: US 9,958,434 B2
(45) Date of Patent: May 1, 2018

(54) FLUORESCENT PROBE SENSING TYROSINE KINASE AND USE THEREOF

(71) Applicant: POSTECH ACADEMY-INDUSTRY FOUNDATION, Pohang-si, Gyeongsangbuk-do (KR)

(72) Inventors: Kyo Han Ahn, Pohang-si (KR); Dokyoung Kim, Geoje-si (KR); Sungjee Kim, Pohang-si (KR); Ki Hean Kim, Pohang-si (KR)

(73) Assignee: POSTECH ACADEMY FOUNDATION, Pohang-si (KR)

( * ) Notice: Subject to any disclaimer, the term of this patent is extended or adjusted under 35 U.S.C. 154(b) by 262 days.

(21) Appl. No.: 14/888,883

(22) PCT Filed: Mar. 10, 2014

(86) PCT No.: PCT/KR2014/001948
§ 371 (c)(1),
(2) Date: Nov. 3, 2015

(87) PCT Pub. No.: WO2014/181960
PCT Pub. Date: Nov. 13, 2014

(65) Prior Publication Data
US 2016/0116455 A1    Apr. 28, 2016

(30) Foreign Application Priority Data
May 10, 2013    (KR) .................. 10-2013-0053252

(51) Int. Cl.
*C12Q 1/48*    (2006.01)
*G01N 33/50*    (2006.01)
(Continued)

(52) U.S. Cl.
CPC ....... *G01N 33/5023* (2013.01); *C07C 223/06* (2013.01); *C09K 11/06* (2013.01);
(Continued)

(58) Field of Classification Search
CPC ........................................ C12Q 1/485
See application file for complete search history.

(56) References Cited

U.S. PATENT DOCUMENTS

2010/0047829 A1    2/2010    Rothe et al.

FOREIGN PATENT DOCUMENTS

KR    10-0963102 B1    6/2010

OTHER PUBLICATIONS

Search of the compound of Formula 1, claim 1, CAS Reg file, Sep. 28, 2017.*

(Continued)

*Primary Examiner* — Rosanne Kosson
(74) *Attorney, Agent, or Firm* — Knobbe Martens Olson & Bear LLP

(57) ABSTRACT

A fluorescent probe for detecting a tyrosine kinase using a compound having an ortho-hydroxy-benzaldehyde structure, and use thereof are provided. The fluorescent probe can show a change in fluorescence when the compound binds with a tyrosine kinase. The compound can be readily synthesized and has high stability and low cytotoxicity in vivo. The fluorescent probe can be used to image cells or tissues overexpressing the tyrosine kinase, the fluorescent probe can be effectively used in a composition for imaging the tissues and a method of imaging the tissues. Also, the fluorescent probe can be used to image cancer cells or tissues since the fluorescent probe can exhibit fluorescence when the fluorescent probe binds to the cancer cells or tissues overexpressing the tyrosine kinase.

6 Claims, 17 Drawing Sheets

(51) Int. Cl.
  *C07C 223/06* (2006.01)
  *G01N 33/574* (2006.01)
  *G01N 33/58* (2006.01)
  *C09K 11/06* (2006.01)

(52) U.S. Cl.
  CPC .......... *C12Q 1/485* (2013.01); *G01N 33/574* (2013.01); *G01N 33/582* (2013.01); *G01N 2333/9121* (2013.01); *G01N 2333/91205* (2013.01); *G01N 2500/10* (2013.01)

(56) References Cited

OTHER PUBLICATIONS

Inae Kim, et al., "Synthesis of -Extended Coumarins and Evaluation of Their Precursors as Reactive Fluorescent Probes for Mercury Ions", Asian Journal of Organic Chemistry, 2012, vol. 1, pp. 60-64.
Samanta, et al., "Spectroscopic probe analysis for exploring probe—protein interaction: A mapping of native, unfolding and refolding of protein bovine serum albumin by extrinsic fluorescence probe", Biophysical Chemistry, 2011, vol. 156, pp. 128-139.
Zeng et al., "Subcellular Localization of Sigma-2 Receptors in Breast Cancer Cells Using Two-Photon and Confocal Microscopy", Cancer Research, 2007, vol. 67, pp. 6708-6716.
Chen et al., "Design and Synthesis of a Fluorescent Reporter of Protein Kinase Activity", Journal of the American Chemical Society, 2002, vol. 124, No. 15, pp. 3840-3841.
Zondlo et al., "Design of an Encodable Tyrosine Kinase-Inducible Domain: Detection of Tyrosine Kinase Activity by Terbium Luminescence", Journal of the American Chemical Society, 2010, vol. 132, No. 16, pp. 5619-5621.
Agnes et al., "Suborganelle Sensing of Mitochondrial cAMP-Dependent Protein Kinase Activity", Journal of the American Chemical Society, 2010, vol. 132, No. 17, pp. 6075-6080.
Rhee et al., "Detection of Kinase Activity Using Versatile Fluorescence Quencher Probes", Angew. Chem. Int. Ed. 2010, vol. 49, pp. 4919-4923.
Vaasa et al., "Small-molecule FRET probes for protein kinase activity monitoring in living cells", Biochemical and Biophysical Research Communications, 2010, vol. 397, pp. 750-755.
Xu et al., "Label-Free Fluorescent Detection of Protein Kinase Activity Based on the Aggregation Behavior of Unmodified Quantum Dots", Analytical Chemistry, 2011, vol. 83, No. 1, pp. 52-59.
Appelblom et al, "Antibody-free lanthanide-based fluorescent probe for determination of protein tyrosine kinase and phosphatase activities", Microchim Acta, 2011, vol. 172, pp. 25-29.
Herbst et al., "Luminescent Kinase Activity Biosensors Based on a Versatile Bimolecular Switch", Journal of the American Chemical Society, 2011, vol. 133, pp. 5676-5679.
Seong et al., "Detection of focal adhesion kinase activation at membrane microdomains by fluorescence resonance energy transfer", Nature Communications, 2011.
Lawrence et al., "Seeing Is Believing: Peptide-Based Fluorescent Sensors of Protein Tyrosine Kinase Activity", ChemBioChem, 2007, vol. 8, pp. 373-378.
Tremblay et al., "A Luminescent Sensor for Tyrosine Phosphorylation", Organic Letters, 2008, vol. 10, No. 1, pp. 5-8.
Sahoo et al., "Single-Label Kinase and Phosphatase Assays for Tyrosine Phosphorylation Using Nanosecond Time-Resolved Fluorescence Detection", Journal of the American Chemical Society, 2007, vol. 129, pp. 15927-15934.
Akiba et al., "Binuclear Terbium (III) Complex as a Probe for Tyrosine Phosphorylation", Chemistry A European Journal, 2010, vol. 16, pp. 5018-5025.
Shults et al., "Versatile Fluorescence Probes of Protein Kinase Activity", Journal of the American Chemical Society, 2003, vol. 125, pp. 14248-14249.
Kikuchi et al., "Anion Sensor-Based Ratiometric Peptide Probe for Protein Kinase Activity", Organic Letters, 2009, vol. 11, No. 13, pp. 2732-2735.
Ojida et al., "Molecular Recognition and Fluorescence Sensing of Monophosphorylated Peptides in Aqueous Solution by Bis(zinc(II)-dipicolylamine)-Based Artificial Receptors", Journal of the American Chemical Society, 2004, vol. 126, pp. 2454-2463.
Wang et al., "Phosphorylation-Driven Protein-Protein Interactions: A Protein Kinase Sensing System", Journal of the American Chemical Society, 2005, vol. 127, pp. 7684-7685.
Sharma et al., "Deep Quench: An Expanded Dynamic Range for Protein Kinase Sensors", Journal of the American Chemical Society, 2007, vol. 129, pp. 2742-2743.
International Search Report dated Jun. 20, 2014 of PCT/KR2014/001948 which is the parent application and its English translation—5 pages.

* cited by examiner

FIG. 3A

| KINOMEscan Gene Symbol | Entrez Gene Symbol | Percent Control % | KINOMEscan Gene Symbol | Entrez Gene Symbol | Percent Control % |
|---|---|---|---|---|---|
| ABL1(E255K)-phosphorylated | ABL1 | 100 | ERBB2 | ERBB2 | 96 |
| ABL1(T315I)-phosphorylated | ABL1 | 89 | ERBB4 | ERBB4 | 100 |
| ABL1-phosphorylated | ABL1 | 57 | ERK1 | MAPK3 | 100 |
| ACVR1B | ACVR1B | 100 | FAK | PTK2 | 89 |
| ADCK3 | CABC1 | 81 | FGFR2 | FGFR2 | 100 |
| AKT1 | AKT1 | 100 | FGFR3 | FGFR3 | 91 |
| AKT2 | AKT2 | 78 | FLT3 | FLT3 | 96 |
| ALK | ALK | 90 | GSK3B | GSK3B | 68 |
| AURKA | AURKA | 100 | IGF1R | IGF1R | 100 |
| AURKB | AURKB | 83 | IKK-alpha | CHUK | 100 |
| AXL | AXL | 100 | IKK-beta | IKBKB | 100 |
| BMPR2 | BMPR2 | 83 | INSR | INSR | 78 |
| BRAF | BRAF | 89 | JAK2(JH1domain-catalytic) | JAK2 | 100 |
| BRAF(V600E) | BRAF | 60 | JAK3(JH1domain-catalytic) | JAK3 | 59 |
| BTK | BTK | 58 | JNK1 | MAPK8 | 82 |
| CDK11 | CDK19 | 100 | JNK2 | MAPK9 | 66 |
| CDK2 | CDK2 | 100 | JNK3 | MAPK10 | 62 |
| CDK3 | CDK3 | 96 | KIT | KIT | 94 |
| CDK7 | CDK7 | 66 | KIT(D816V) | KIT | 82 |
| CDK9 | CDK9 | 100 | KIT(V559D,T670I) | KIT | 100 |
| CHEK1 | CHEK1 | 100 | LKB1 | STK11 | 100 |
| CSF1R | CSF1R | 100 | MAP3K4 | MAP3K4 | 78 |
| CSNK1D | CSNK1D | 94 | MAPKAPK2 | MAPKAPK2 | 92 |
| CSNK1G2 | CSNK1G2 | 100 | MARK3 | MARK3 | 100 |

FIG. 3B

| KINOMEscan Gene Symbol | Entrez Gene Symbol | Percent Control (a) | KINOMEscan Gene Symbol | Entrez Gene Symbol | Percent Control (a) |
|---|---|---|---|---|---|
| MET | MET | 100 | PKAC-alpha | PRKACA | 94 |
| MKNK1 | MKNK1 | 72 | PLK1 | PLK1 | 81 |
| MKNK2 | MKNK2 | 55 | PLK3 | PLK3 | 87 |
| MLK1 | MAP3K9 | 100 | PLK4 | PLK4 | 71 |
| p38-alpha | MAPK14 | 100 | PRKCE | PRKCE | 63 |
| p38-beta | MAPK11 | 100 | RAF1 | RAF1 | 100 |
| PAK1 | PAK1 | 100 | RET | RET | 82 |
| PAK2 | PAK2 | 100 | ROCK2 | ROCK2 | 74 |
| PAK4 | PAK4 | 100 | ROCK3 | ROCK2 | 100 |
| PCTK1 | CDK16 | 78 | RSK2 (Kin.Dom.1-N-terminal) | RPS6KA3 | 49 |
| PDGFRA | PDGFRA | 31 | SNARK | NUAK2 | 88 |
| PDGFRB | PDGFRB | 100 | SRC | SRC | 100 |
| PDPK1 | PDPK1 | 92 | SRPK3 | SRPK3 | 100 |
| PIK3C2B | PIK3C2B | 63 | TGFBR1 | TGFBR1 | 100 |
| PIK3CA | PIK3CA | 93 | TIE2 | TEK | 97 |
| PIK3CG | PIK3CG | 82 | TRKA | NTRK1 | 100 |
| PIM1 | PIM1 | 100 | TSSK1B | TSSK1B | 53 |
| PIM2 | PIM2 | 94 | TYK2(JH1domain-catalytic) | TYK2 | 44 |
| PIM3 | PIM3 | 95 | ULK2 | ULK2 | 91 |
| YANK3 | STK32C | 68 | VEGFR2 | KDR | 90 |
| ZAP70 | ZAP70 | 79 | | | |
| DCAMKL1 | DCLK1 | 85 | MEK1 | MAP2K1 | 88 |
| DYRK1B | DYRK1B | 100 | MEK2 | MAP2K2 | 100 |
| EGFR | EGFR | 70 | MET | MET | 100 |
| EGFR(L858R) | EGFR | 64 | MKNK1 | MKNK1 | 72 |
| EPHA2 | EPHA2 | 100 | MKNK2 | MKNK2 | 55 |

FLUORESCENT PROBE SENSING TYROSINE KINASE AND USE THEREOF

STATEMENT REGARDING GOVERNMENT RIGHTS

This invention was made with government support of Republic of Korea under Global Research Laboratory Program (NRF-2014K1A1A2064569) awarded by Korean Ministry of Science, ICT and Future Planning.

This invention was made with government support of Republic of Korea under the Korea Health Technology R&D Project (HI13C1378) awarded by Korean Ministry of Health & Welfare.

This invention was made with government support of Republic of Korea under Advanced Research Center Program (NRF-2008-0061892) awarded by Korean Ministry of Science, ICT and Future Planning.

The government has certain rights in the invention.

CROSS-REFERENCE TO RELATED APPLICATION

This application claims priority to and the benefit of Korean Patent Application No. 10-2013-0053252, filed on May 10, 2013, the disclosure of which is incorporated herein by reference in its entirety.

FIELD

The present invention relates to a fluorescent probe for selectively detecting a tyrosine kinase, and use thereof.

BACKGROUND

A kinase is an enzyme that plays the most important role in regulating in vivo signal transduction systems. Protein kinase enzymes take charge of in vivo signal transduction by transferring a γ-phosphate group of adenosine 5'-triphosphate (ATP) to a substrate protein. Protein kinase enzymes are classified with tyrosine kinases and serine/threonine kinases. More than 500 kinase enzymes have been found so far (G. Manning et al, *Science* 2002, 298, 1912).

A tyrosine kinase functions to phosphorylate a hydroxyl (—OH) group of a tyrosine residue and take complete charge of functions of in vivo signal transduction systems. When such a kinase enzyme is overexpressed, or overactivated by mutation, various diseases (cancer, diabetes, inflammation, brain disease, etc.) are caused. A living body should harmoniously turn on/off cell signal transduction systems in order to maintain homeostasis. In this case, when signal transduction does not continue to be regulated due to overactivities of certain protein kinase enzymes, diseases such as cancer are caused (P. B. Jensen and T. Hunter, *Nature* 2001, 411, 355.). Therefore, a molecular probe capable of effectively detecting the activities of certain kinase enzymes is of very high importance since it can be used to diagnose diseases including cancer. Also, such a molecular probe is used to search for a drug having an action mechanism to inhibit the activities of certain overactivated protein kinase enzymes, and thus has a very important situation to develop a new drug.

A method including a series of processes has been known as a method of measuring the presence, overexpression, and activities of such a protein kinase enzyme, but its analytic process is complicated and is also not a method of directly detecting a kinase enzyme but an indirect method of detecting compounds associated with a phosphorylation process, such as ATP. Among these compounds, a fluorescent molecular probe has an advantage in that it can easily detect activities of a kinase enzyme with high sensitivity.

Conventional kinase enzyme fluorescent probes have a very complicated structure. That is, they have a structure in which a fluorophore is introduced into a peptide chain which can be recognized by a kinase enzyme, but have a problem in that it is very difficult to select a suitable fluorophore to cause a change in fluorescence when the enzyme interacts with the peptide chain and to spatially arrange the fluorophore.

Fluorescent probes that can measure the activities of the protein kinase enzymes reported so far have a peptide chain containing a tyrosine residue which can be recognized by the enzyme as described above, and often include a lanthanide metal complex or an organic fluorophore having a complicated structure (Chen. C. et al., *J. Am. Chem. Soc.* 2001, 124, 3840; Zondlo. S. C. et al., *J. Am. Chem. Soc.* 2010, 132, 5619; Agnes. R. S. et al., *J. Am. Chem. Soc.* 2010, 132, 6075; Rhee. H. et al., *Angew. Chem. Int. Ed.* 2010, 49, 4919; Vaasa. A. et al., *Biochemistry and Biophysical Research Communication.* 2010, 397, 750; Xu. X. et al., *Anal. Chem.* 2011, 83, 52; Appelblom. H. et al., *Microchim. Acta.* 2011, 172, 25; Herbst. K. J. et al., *J. Am. Chem. Soc.* 2011, 133, 5676; Seong. J. *Nat. Comm.* 2011, DOI:10.1038/ncomms1414; Lawrence. D. S. *Chem Bio Chem.* 2007, 8, 373; Tremblay. M. S. et al., *Org. Lett.* 2008, 10, 5; Sahoo. H. et al., *J. Am. Chem. Soc.* 2007, 129, 15927; Akiba. H. et al., *Chem. Eur. J.* 2010, 16, 5018; Shults. M. D. et al., *J. Am. Chem. Soc.* 2003, 125, 14248; Kikuchi. K. et al., *Org. Lett.* 2009, 11, 2732; Ojida. A. et al., *J. Am. Chem. Soc.* 2004, 126, 2454; Wang. Q. et al., *J. Am. Chem. Soc.* 2005, 127, 7684; Sharma. V. et al., *J. Am. Chem. Soc.* 2007, 129, 2742).

Also, since the conventional fluorescent probes used to detect a tyrosine kinase includes not only a peptide substrate recognizing the enzyme but a luminophore having a complicated structure to present a fluorescence signal upon recognition of the enzyme, they have a high molecular weight, and a synthesis process is complicated. First of all, when the conventional fluorescent probes detect kinase enzymes in cells or tissues, stability and interference by other compounds may become of a concern, which leads to limitation on their use.

The probes which emit fluorescence when they encounter a certain kinase enzyme as a small molecule still have highly challenging issues in spite of their importance. It is not reported so far that the fluorescent probes can directly detect the presence, overexpression, or activities of the kinase enzyme.

Therefore, the present inventors have developed an epoch-making fluorescent probe, which emits fluorescence through interaction with a tyrosine kinase enzyme in vivo, as a small-molecule probe which is easily synthesized and having high stability and low cytotoxicity in vivo. The fluorescent probe has various advantages (such as high tissue permeability, low fluorescence interference from tissues themselves, high resolution, and low cell injury, etc.) since the fluorescent probe can be two-photon excited. It is confirmed that the developed fluorescent probe has a change in fluorescence when it binds to certain kinase enzymes present in cancer cells, and also exhibits fluorescence when it selectively binds to cancer tissues. As a result, the present inventors have found that the fluorescent probe according to the present invention can be used to image the cells or tissues overexpressing a tyrosine kinase, and image the cancer cells or tissues. Therefore, the present invention is completed based on these facts.

SUMMARY OF THE INVENTION

The present invention is directed to a fluorescent probe for detecting a tyrosine kinase using a compound having an ortho-hydroxy-benzaldehyde structure, a method of screening a tyrosine kinase inhibitor using the same, a method of measuring tyrosine kinase activities, and a method of single-photon or two-photon imaging cells.

Also, the present invention is directed to a composition for screening a drug inhibiting overexpression of a tyrosine kinase, including the fluorescent probe.

Further, the present invention is directed to a composition capable of imaging cells or tissues overexpressing a tyrosine kinase, including the fluorescent probe, and a method of imaging cells or tissues.

However, the above and other objects, features, and advantages of the present invention will become more apparent to those of ordinary skill in the art by describing in detail embodiments thereof.

According to an aspect of the present invention, there is provided a fluorescent probe for detecting a tyrosine kinase using a compound represented by the following Formula 1, or an analogue thereof.

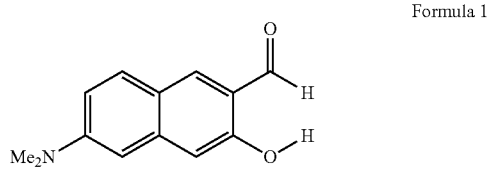 [SMILES: CN(C)c1ccc2cc(C=O)c(O)cc2c1]

Formula 1

According to one embodiment of the present invention, the compound may have an ortho-hydroxy-benzaldehyde structure.

According to another embodiment of the present invention, the compound may exhibit fluorescence by breaking an intramolecular hydrogen bond in the ortho-hydroxy-benzaldehyde structure when the compound binds to a tyrosine kinase.

According to still another embodiment of the present invention, the tyrosine kinase may be selected from the group consisting of ABL1 (T315I), BRAF, PDGFRa, RSK2, TYK2, and Src.

According to another aspect of the present invention, there is provided a method of screening a tyrosine kinase inhibitor using the fluorescent probe according to the present invention.

According to still another aspect of the present invention, there is provided a method of measuring tyrosine kinase activities using the fluorescent probe according to the present invention.

According to still another aspect of the present invention, there is provided a method of single-photon or two-photon imaging cells using the fluorescent probe according to the present invention.

According to still another aspect of the present invention, there is provided a composition for screening a drug inhibiting overexpression of a tyrosine kinase, which includes the fluorescent probe according to the present invention.

According to still another aspect of the present invention, there is provided a composition for imaging cells or tissues overexpressing a tyrosine kinase, which includes the fluorescent probe according to the present invention.

According to one embodiment of the present invention, the cells or tissues overexpressing the tyrosine kinase may be cancer cells, or cancer tissues.

According to yet another aspect of the present invention, there is provided a method of imaging cells or tissues overexpressing a tyrosine kinase, which includes measuring fluorescence in the cells or tissues using the fluorescent probe according to the present invention.

According to one embodiment of the present invention, the cells or tissues overexpressing the tyrosine kinase may be cancer cells, or cancer tissues.

According to another embodiment of the present invention, the measuring of the fluorescence may be performed using one or more apparatus selected from the group consisting of a confocal fluorescence microscope, a two-photon fluorescence microscope, and an optical coherence tomograph.

BRIEF DESCRIPTION OF THE DRAWINGS

The above and other objects, features, and advantages of the present invention will become more apparent to those of ordinary skill in the art by describing in detail embodiments thereof with reference to the accompanying drawings, in which:

FIGS. 3A and 3B show the results obtained by determining the binding selectivities of compound 1 to 96 kinase enzymes;

DETAILED DESCRIPTION OF EMBODIMENTS

Figure 1:
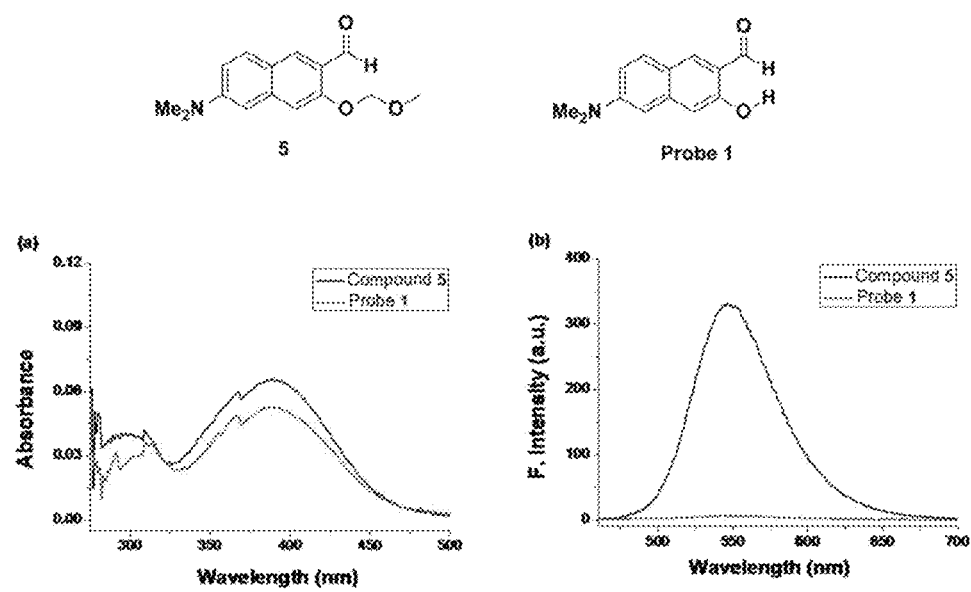
FIG. 1 is a graph illustrating absorbance and fluorescence of compound 1.

Embodiments of the present invention will be described in detail below with reference to the accompanying drawings. While the present invention is shown and described in connection with embodiments thereof, it will be apparent to those skilled in the art that various modifications can be made without departing from the scope of the invention.

The present inventors have made ardent attempts to develop a fluorescent molecular probe capable of readily detecting a tyrosine kinase enzyme in cells or tissues, designed a molecular probe capable of causing a change in optical properties when a hydroxyl group binds to an enzyme, for example, to form a hydrogen bond, based on the fact that an aryl hydroxyl group participates in an enzymatic reaction of a tyrosine kinase, and developed a fluorescent probe of the present invention, based on the fact that the molecular probe binds to certain kinase enzymes to cause a change in fluorescence.

The present invention provides a fluorescent probe for detecting a tyrosine kinase using a compound represented by the following Formula 1, or an analogue thereof Formula 1

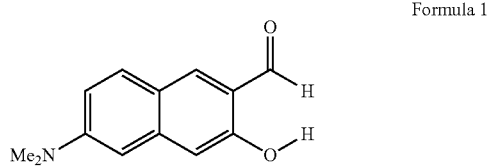 [SMILES: CN(C)c1ccc2cc(C=O)c(O)cc2c1]

According to one embodiment of the present invention, the compound may have an ortho-hydroxy-benzaldehyde structure.

Also, the compound may exhibit fluorescence when the compound binds to a tyrosine kinase to break an intramolecular hydrogen bond in the ortho-hydroxy-benzaldehyde structure.

In addition, the tyrosine kinase may be selected from the group consisting of ABL1 (T315I), BRAF, PDGFRa, RSK2, TYK2, and Src, but the present invention is not limited thereto.

In the compound of Formula 1 developed in the present invention, a hydroxyl (—OH) functional group at a $3^{rd}$ position thereof reacts with an aldehyde (—CHO) functional group at a $2^{nd}$ position thereof to form an intramolecular hydrogen bond. In this situation, the compound of Formula 1 does not emit fluorescence, but has a unique luminescence characteristic in which fluorescence is emitted when the compound binds to a certain tyrosine kinase enzyme to break the intramolecular hydrogen bond and form an intermolecular hydrogen bond with a neighboring functional group of the enzyme. Also, it could be seen that the two-photon fluorescent probe according to the present invention may be used to easily determine the presence and activities of six kinase enzymes (ABL1 (T315I), BRAF, PDGFRa, RSK2, TYK2, and Src) by allowing the two-photon fluorescent probe to bind to the kinase enzymes so as to cause an increase in fluorescence intensity (see FIGS. 2 to 7). These characteristics may be implemented by introducing an intramolecular hydrogen bond into the characteristics of a fluorophore having an electron donor-electron acceptor structure.

Also, the present invention provides a method of screening a tyrosine kinase inhibitor using the fluorescent probe according to the present invention.

In addition, the present invention provides a method of measuring tyrosine kinase activities using the fluorescent probe according to the present invention.

Further, the present invention provides a method of single-photon or two-photon imaging cells using the fluorescent probe according to the present invention.

According to one embodiment of the present invention, when the compound of Formula 1 developed in the present invention is used as the fluorescent probe, it could be seen that the compound of Formula 1 has selective binding affinity to kinase enzymes and an ability to inhibit activities of the kinase enzymes. From these results, it could be seen that the fluorescent probe according to the present invention may be effectively used in a method of determining the presence and activities of a kinase enzyme, a method of detecting an inhibitor, and a method of imaging cells by allowing the fluorescent probe to bind to the kinase enzymes (ABL1 (T315I), BRAF, PDGFRa, RSK2, TYK2, and Src) to cause an increase in fluorescence intensity (see FIGS. 2 and 11).

Also, the present invention provides a composition for screening a drug inhibiting overexpression of a tyrosine kinase, which includes the fluorescent probe according to the present invention.

In still another aspect, the present invention provides a method of screening a drug inhibiting overexpression of a tyrosine kinase, which includes:

1) allowing the fluorescent probe of the present invention to react with a tyrosine kinase alone or in combination of a drug candidate;

2) detecting fluorescence emitted in step (1); and 3) assaying binding affinity of the drug candidate to the tyrosine kinase by comparing the fluorescence detected in step (2).

In this case, when a level of fluorescence obtained when the fluorescent probe of the present invention reacts with the tyrosine kinase in connection with the drug candidate is reduced, compared to that obtained when the fluorescent probe reacts with the tyrosine kinase alone, the drug candidate may be decided to be a drug inhibiting overexpression of a tyrosine kinase.

The detecting of the fluorescence may be performed using one or more apparatus selected from the group consisting of a confocal fluorescence microscope, a two-photon fluorescence microscope, and an optical coherence tomograph, but the present invention is not limited thereto.

The drug candidate may include various compounds, proteins, and nucleic acids, but the present invention is not limited thereto.

Also, the present invention provides a composition for imaging cells or tissues overexpressing a tyrosine kinase, which includes the fluorescent probe according to the present invention.

In addition, the present invention provides a method of imaging cells or tissues overexpressing a tyrosine kinase, which includes measuring fluorescence in the cells or tissues using the fluorescent probe according to the present invention.

The cells or tissues overexpressing the tyrosine kinase may be cancer cells, or cancer tissues, but the present invention is not limited thereto.

The measuring of the fluorescence may be performed using one or more apparatus selected from the group consisting of a confocal fluorescence microscope, a two-photon fluorescence microscope, and an optical coherence tomograph, but the present invention is not limited thereto.

According to one embodiment of the present invention, the compound of Formula 1 developed in the present invention is used as the fluorescent probe to determine photophysical properties, selective binding affinity to kinase enzymes, and ability to inhibit kinase enzyme activities, conduct proton nuclear magnetic resonance (NMR) studies, and perform one-photon confocal microscopy imaging on cancer cell lines, two-photon microscopy imaging on cancer cell lines, and in vivo two-photon microscopy and OCT imaging on a mouse tumor model. As a result, it could be seen that the fluorescent probe according to the present invention selectively shows a fluorescence turn-on response in cancer tissues overexpressing the tyrosine kinase (see FIGS. 1 to 16).

Therefore, the fluorescent probe according to the present invention may be effectively used for a composition for imaging cells or tissues overexpressing a tyrosine kinase, or used in a method of imaging cells or tissues.

The content of the fluorescent probe as an active ingredient in the composition for imaging cells or tissues may be properly adjusted according to the use type and purpose, the severity of patients, etc. For example, the content of the fluorescent probe may be in a range of 1 to 20 mg/kg, preferably 5 to 10 mg/kg, and most preferably 10 mg/kg, but the present invention is not limited thereto.

The composition for imaging cells or tissues may be administered to mammals including human beings via various routes of administration. An administration method may be all kinds of methods widely used in the related art. For example, the composition for imaging cells or tissues may be administered orally, rectally, or intravenously, or administered by means of intramuscular, subcutaneous, intracervical or intracerebroventricular injection. The composition according to the present invention may be prepared into an oral formulation in the form of a powder, a tablet, a capsule, a suspension, an emulsion, and the like, or a parenteral formulation in the form of a patch, a suppository, and a sterile injectable solution according to conventional methods.

Hereinafter, embodiments are presented to aid in understanding the present invention. However, it should be understood that the following embodiments are given by way of illustration of the present invention only, and are not intended to limit the scope of the present invention.

EXAMPLE 1

Synthesis and Structure Analysis of Compound 1

To develop a molecular probe capable of causing a change in optical properties when a hydroxyl group binds to an enzyme, for example, to form a hydrogen bond, based on the fact that an aryl hydroxyl group participates in an enzymatic reaction of a tyrosine kinase, the present inventors synthesized the compound of Formula 1 according to the following Scheme 1.

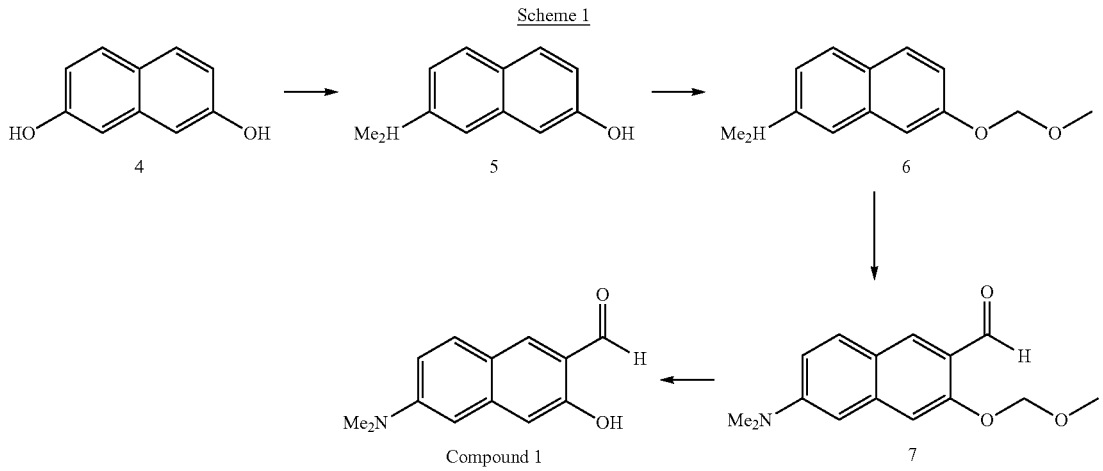

Scheme 1

(1) Synthesis of 7-(dimethylamino)naphthalen-2-ol (compound 5 in Scheme 1)

The present inventors performed synthesis of 7-(dimethylamino)naphthalen-2-ol.

Water ($H_2O$, 8 mL) and an aqueous dimethylamine solution (40% in $H_2O$, 10.5 mL, 93.5 mmol) were put into a sealed tube containing compound 4 (3 g, 18.7 mmol, Sigma-aldrich, D116408), which was a starting material for synthesis, and sodium metabisulfite ($Na_2S_2O_5$, 7.11 g, 37.4 mmol), and the tube was sealed. The resulting mixture was stirred at 150° C. for 8 hours in a silicone oil tube. Thereafter, a reaction product was cooled to room temperature (25° C.), the tube was opened, and dichloromethane (100 mL), water (100 mL), and saturated brine (30 mL) were put into the tube to extract an organic layer through a separatory funnel. The organic layer was dried on anhydrous sodium sulfate ($Na_2SO_4$, 5 g), and concentrated using an aspirator (25° C., 20 to 500 mmHg). The light brown solid compound obtained thus was separated (developing solution: 20% EtOAc/hexane) through column chromatography (diameter: 6 cm, and height: 15 cm) using silica gel (Merck-silicagel 60, 230-400 mesh) to obtain a white solid compound 5 (2.10 g, 60%). The product had a developing value of $R_f$=0.25

(20% EtOAc/hexane—developing once), as analyzed through thin layer chromatography (TLC, silica gel 60E-254 glass plate, Merck). $^1$H NMR (CDCl$_3$, 300 MHz, 293K): δ 7.66-7.59 (m, 2H), 7.05-7.02 (m, 1H), 6.96-6.95 (d, 1H), 6.85-6.82 (m, 1H), 6.78-6.77 (d, 1H), 5.10 (s, 1H), 3.05 (s, 6H). $^{13}$C NMR (CDCl$_3$, 75 MHz, 293K): δ153.88, 149.17, 136.24, 129.39, 128.61, 122.44, 114.22, 113.80, 108.02, 105.32, 40.91. HRMS: m/z calcd. for C$_{12}$H$_{13}$NO 187.0997 found 187.0999.

(2) Synthesis of 7-(methoxymethoxy)-N,N-dimethyl-naphthalen-2-amine (compound 6 in Scheme 1)

The present inventors performed synthesis of 7-(methoxymethoxy)-N,N-dimethylnaphthalen-2-amine.

More particularly, sodium hydride (NaH, 235 mg, 5.875 mmol) was added to a solvent, N,N-dimethylformamide (DMF, 5 mL), and an argon balloon was then placed. Then, the resulting mixture was cooled to −15° C. using saturated brine and ice. Compound 5 (1 g, 5.34 mmol) was dissolved in DMF (5 mL), and then added dropwise to the mixture at a constant temperature for approximately 5 minutes. H$_2$ gas generated in this procedure is exhausted through a silicone oil trap. The mixture was stirred at the same temperature for an hour, and it was confirmed that bubbles (H$_2$ gas) were not formed in the trap. Subsequently, chloromethyl methyl ether (0.4 mL, 5.34 mmol) was added dropwise for approximately 5 minutes. When the injection was completed, the resulting mixture was cooled to room temperature (25° C.), and stirred for 6 hours. After 6 hours, water (100 mL) was added, and the mixture was extracted with ethyl acetate (EtOAc, 200 mL). The extracted organic layer (EtOAc) was dried on anhydrous sodium sulfate (10 g) to remove water remaining in the organic layer. The organic layer was concentrated using an aspirator. The light brown liquid compound obtained thus was separated (developing solution: 5% EtOAc/hexane) through column chromatography (diameter: 6 cm, and height: 15 cm) using silica gel to obtain white solid compound 6 (988 mg, 80%). The product had a developing value of R$_f$=0.45 (20% EtOAc/hexane—developing once), as analyzed through TLC. $^1$H NMR (CDCl$_3$, 300 MHz, 293K): δ 7.75 (d, 1H), 7.72 (d, 1H), 7.40-7.39 (d, 1H), 7.15-7.08 (m, 2H), 6.98-6.97 (d, 1H), 5.39 (s, 2H), 3.69 (s, 3H), 3.11 (s, 6H). $^{13}$C NMR (CDCl$_3$, 75 MHz, 293K): δ 155.75, 149.16, 136.23, 129.11, 128.55, 123.00, 114.99, 114.58, 108.69, 105.96, 94.62, 56.07, 40.83. HRMS: m/z calcd. for C$_{14}$H$_{17}$NO$_2$ 231.1259 found 231.1262.

(3) Synthesis of 6-(dimethylamino)-3-(methoxymethoxy)-2-naphthaldehyde

The present inventors performed synthesis of 6-(dimethylamino)-3-(methoxymethoxy)-2-naphthaldehyde (compound 7 in Scheme 1).

More particularly, compound 6 (2.2606 g, 9.774 mmol) was put into a 100 mL round-bottom flask, and an argon balloon was then placed. Thereafter, ethyl ether (Et$_2$O, 50 mL) was added, and the resulting mixture was cooled to −20° C. using saturated brine and ice. After the temperature was checked, tertiary butyl lithium (tert-BuLi, 8.6 mL, 14.66 mmol) was added dropwise for approximately 30 minutes. In this case, the color of the mixture turned dark brown. When the injection was completed, the mixture was stirred at the same temperature for 2 hours. After the 2 hour stirring, DMF (1.3 mL, 16.62 mmol) was added dropwise for approximately 5 minutes. When the injection was completed, the mixture was stirred at the same temperature for an hour. In this case, the mixture turned light yellow. After the one hour stirring, 4N HCl (10 mL) and primarily distilled water (10 mL) were added, and the resulting mixture was stirred for 10 minutes. After 10 minutes, the mixture was extracted with EtOAc (300 mL), saturated brine (100 mL), and water (200 mL). The organic layer (EtOAc) obtained through the extraction was dried on anhydrous sodium sulfate (15 g) to remove water remaining in the organic layer, and concentrated using an aspirator. The light yellow solid compound obtained thus was separated (developing solution: 20% EtOAc/hexane) through column chromatography (diameter: 6 cm, and height: 15 cm) using silica gel to obtain light yellow solid compound 7 (1.27 g, 50%). The product had a developing value of R$_f$=0.25 (20% EtOAc/hexane—developing once), as analyzed through TLC. $^1$H NMR (CDCl$_3$, 300 MHz, 293K): δ 10.49 (s, 1H), 8.25 (s, 1H), 7.75-7.73 (d, 1H), 7.29-7.24 (d, 1H), 7.05-7.03 (dd, 1H), 6.77-6.76 (d, 1H), 5.40 (s, 2H), 3.59 (s, 3H), 3.12 (s, 6H). $^{13}$C NMR (CDCl$_3$, 75 MHz, 293K): δ 189.61, 155.99, 150.71, 139.74, 131.16, 130.89, 122.26, 121.29, 114.76, 107.66, 104.30, 94.75, 56.39, 40.32. HRMS: m/z calcd. for C$_{15}$H$_{17}$NO$_3$ 259.1208 found 259.1211.

(4) Synthesis of 6-(dimethylamino)-3-hydroxyl-2-naphthaldehyde (compound of Formula 1)

The present inventors performed synthesis of 6-(dimethylamino)-3-hydroxyl-2-naphthaldehyde.

More particularly, compound 7 (195 mg, 0.75 mmol), isopropyl alcohol (10 mL), and 5M HCl (5 mL) were put into a 25 mL round-bottom flask, and then stirred at 60° C. for 3 hours. After 3 hours, the flask was cooled at room temperature, and isopropyl alcohol was then removed in an aspirator. Thereafter, the resulting mixture was extracted with ethyl acetate (100 mL) and water (100 mL). The organic layer (EtOAc) obtained through the extraction was dried on anhydrous sodium sulfate (3 g) to remove water remaining in the organic layer, and then concentrated using an aspirator. The yellow solid compound obtained thus was separated (developing solution: 20% EtOAc/hexane) through column chromatography (diameter: 2 cm, and height: 15 cm) using silica gel to obtain a yellow solid compound of Formula 1 (113 mg, 70%). The product had a developing value of R$_f$=0.35 (20% EtOAc/hexane—developing once), as analyzed through TLC. $^1$H NMR (CDCl$_3$, 300 MHz, 293K): δ 10.54 (s, 1H), 9.89 (s, 1H), 7.90 (s, 1H), 7.70-7.67 (d, 1H), 7.02-6.98 (m, 2H), 6.66-6.65 (d, 1H), 3.13 (s, 6H). $^{13}$C NMR (CDCl$_3$, 75 MHz, 293K): δ 195.26, 156.83, 151.39, 140.62, 137.75, 130.87, 120.63, 119.03, 114.18, 108.73, 103.22, 40.26. HRMS: m/z calcd. for C$_{13}$H$_{13}$NO$_2$ 215.0946 found 259.0946.

In this case, the compound of Formula 1 developed in the present invention was named "compound 1."

EXAMPLE 2

Absorbance and Photophysical Properties of Compound 1

The present inventors measured absorbance and a change in fluorescence of compound 1 under various solvent conditions. The results are shown in FIG. 1.

The present inventors measured the absorbance and fluorescence of compound 1 in a buffer (pH 7.5, 10 mM HEPES). A UV/Vis spectrophotometer commercially available from HP was used to analyze the UV/Vis absorption spectra, and a photon technical international fluorescence system commercially available from PTI was used to analyze the fluorescence spectra. In this case, a cell used when compound 1 was put into each type of equipment was a standard quartz cell having a thickness of 1 cm.

In addition to compound 1, compound 5 was shown as a reference material in FIG. 1. In this case, compound 5 is a reference material obtained by introducing an alkyl group into a —OH group of compound 1 to remove an intramolecular hydrogen bond.

The panels (a) and (b) of the graph show the absorbances and fluorescence intensities of compound 5 and compound 1 under a solvent condition (for example, a 10 mM HEPES buffer, pH 7.5). The absorption spectra (a) under the solvent condition of a HEPES buffer showed that both the compounds had the maximum absorbance values at 390 nm. However, the fluorescence spectra (b) showed that compound 5 emitted strong fluorescence at 550 nm, but compound 1 did not emit fluorescence.

EXAMPLE 3

Protein Binding Selectivity of Compound 1

The present inventors confirmed the protein binding selectivity of compound 1 by means of a change in fluorescence. The results are shown in FIG. 2.

More particularly, to determine whether compound 1 selectively binds to a kinase enzyme, various proteins (including a kinase enzyme) were used to check a change in fluorescence. In this experiment, a buffer (100 mM HEPES buffer, pH 7.4) was used as the solvent, and a kinase commercially available from Carna Biosciences was used as the kinase enzyme. Here, each kinase enzyme was stored at −80° C. together with a solvent (50 mM Tris-HCl, 150 mM NaCl, 0.1% CHAPS, 1 mM DTT, and 10% Glycerol, pH 7.5) kindly provided by the manufacturer. ATP and $MgCl_2$ used herein were commercially available from Sigma, and Gleevec commercially available from Selleck Chemicals was used as the kinase inhibitor. A 96-well fluorescence assay plate (commercially available from SPL Life Science) was used as a plate used upon measurement of fluorescence, and a VCITOR 3 multilabel counter (commercially available from Perkin Elmer-Wellesley) was used as a measuring machine. A 355 nm-thick filter was used to produce excitation wavelengths of the measuring machine, and a 535 nm-thick filter was used to produce emission wavelengths of the measuring machine. Stirring was performed at 37° C. for 24 hours at a rotary speed of 170 rpm using an NB-205Q model (commercially available from N-BIOTEK). Compound 1 was dissolved in a DMSO solution (1 mM, 10 mM, 50 mM, 100 mM, and 200 mM) to be used, and DMSO in every tube was adjusted to be substantially the same content (less than 1%) under the finally used solvent conditions. $Mg^{2+}$ and ATP were used at a content of 1 mM.

Figure 2:
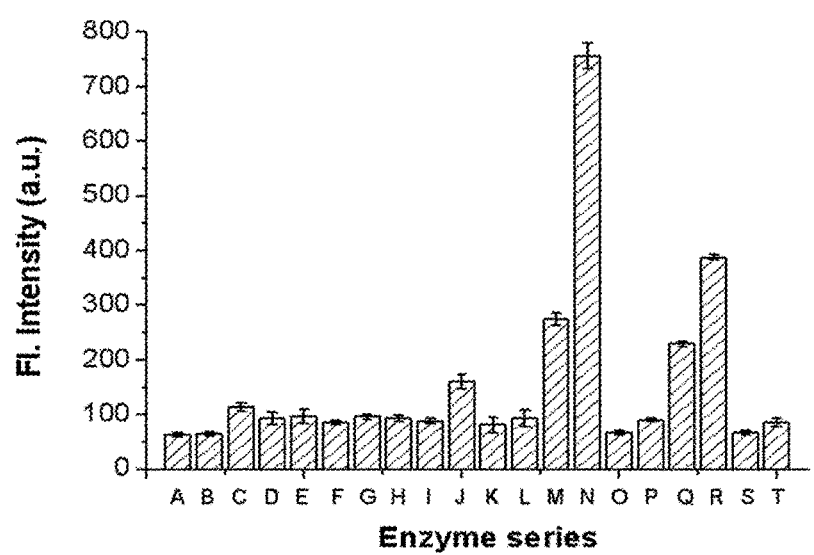
FIG. 2 is a graph illustrating the results of protein binding selectivity of compound 1 obtained by measuring fluorescence intensity of compound 1.

In the graph shown in FIG. 2, the horizontal axis represents kinds of proteins, and the vertical axis represents fluorescence intensities of the proteins. Each experimental value was basically an average value of three experiments conducted through the same course for preparing for experiments, a concentration of compound 1 used was 100 μM, and an amount of each protein was 0.2 μg/mL. The kinds of proteins indicated on the horizontal axis are as follows. In this case, compound 1 was expressed as Probe 1 in the table shown in FIG. 2.

(A) Probe 1;
(B) Probe 1 with Mg and ATP;
(C) Probe 1 with BSA;
(D) Probe 1 with TEV;
(E) Probe 1 with lysozyme;
(F) Probe 1 with creatine kinase;
(G) Probe 1 with ABL (E255K);
(H) Probe 1 with ABL (E255K), Mg, and ATP;
(I) Probe 1 with ABL (T315I);
(J) Probe 1 with ABL (T315I), Mg, and ATP;
(K) Probe 1 with BRAF;
(L) Probe 1 with BRAF, Mg, and ATP;
(M) Probe 1 with PDGFRa;
(N) Probe 1 with PDGFRa, Mg, and ATP;
(O) Probe 1 with RSK2;
(P) Probe 1 with RSK2, Mg, and ATP;
(Q) Probe 1 with Src;
(R) Probe 1 with Src, Mg, and ATP;
(S) Probe 1 with TYK2;
(T) Probe 1 with TYK2, Mg, and ATP As a result, it could be seen that compound 1 showed the highest fluorescence intensity at the enzyme N including PDGFRa kinase and cofactors, Mg and ATP, and thus had significant binding affinity to PDGFRa, as shown in FIG. 2.

In addition, it could be seen that compound 1 was sensitized in the presence of the enzyme R including Src kinase and cofactors, and compound 1 selectively bound to PDGFRa and Src kinase present abundantly in cancer cells to cause an increase in fluorescence.

EXAMPLE 4

Selectivity of Compound 1 to 96 Kinase Enzymes

The present inventors confirmed binding levels of compound 1 to 96 kinase enzymes to determine the selectivities of compound 1 to the kinase enzymes. The results are shown in FIGS. 3A and 3B.

More particularly, to determine selectivities to various kinds of kinase enzymes, the samples were entrusted to DiscoveRX (U.S.A), which was able to determine the binding affinities to a total of 96 kinase enzymes, to perform KINOMEscan experiments. This company treated all kinds of information on the entrusted samples as confidential, and analyzed the sample with charge. Compound 1 was provided to the company, and the company performed the KINOMEscan experiments, and provided the results (DiscoveRX corp.)

KINOMEscan is an experiment in which compound 1 and a compound (a material strongly binding to kinase enzymes) competing for compound 1 are treated with a kinase enzyme at the same time to determine how many the competing compound binds to active sites of the kinase enzymes, compared with compound 1. In this experiment, an experimental value is expressed as a percentile value. In this case, a lower percentile value means that compound 1 more strongly bind to the kinase enzymes.

As a result, it could be seen that compound 1 bound to at least 50 of a total of the 96 kinase enzymes, as shown in FIG. 3. In particular, it was confirmed that compound 1 has a low percentile value with respect to ABL1 (T315I), BRAF, PDGFRa, RSK2, and TYK2.

From these results, it could be seen that compound 1 showed selectivity to the five kinase enzymes, and that compound 1 strongly bound to the PDGFRa kinase enzyme and an increase in fluorescence intensity was caused, compared to the results of Example 4.

EXAMPLE 5

Inhibitory Ability of Compound 1 to Inhibit Activities of Kinase Enzyme

The present inventors confirmed the inhibitory abilities of compound 1 to inhibit the activities of the kinase enzymes screened in Example 4. The results are shown in FIG. 4.

More particularly, kinase activity inhibition screening on inhibitory abilities of compound 1 to inhibit enzymatic activities of the Src kinase enzyme showing an increase in fluorescence in Example 3 in addition to the five kinase enzymes having a low percentile value in Example 4 was performed. The samples were entrusted to Reaction Biology Corp. (RBC, U.S.A) to perform this experiment. This company treated all kinds of information on the entrusted samples as confidential, and analyzed the sample with charge.

Figure 4:
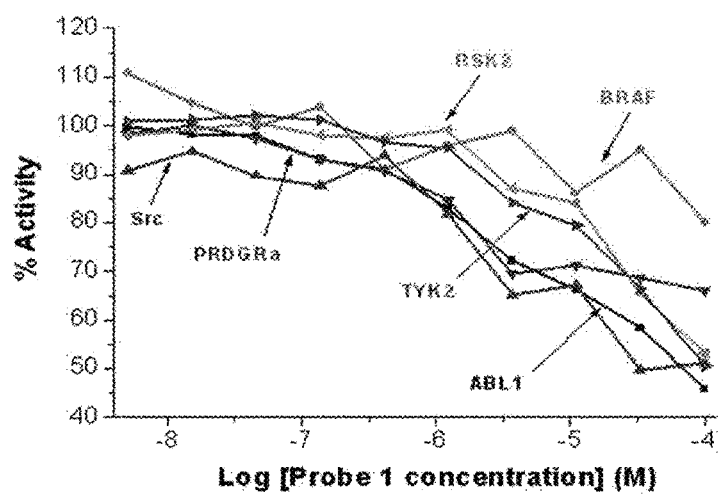
FIG. 4 shows the results obtained by measuring inhibitory abilities of compound 1 to inhibit the activities of the 6 finally selected kinase enzymes which are confirmed to show binding selectivity to compound 1.

Here, an experimental value is expressed as $IC_{50}$ (inhibition concentration for 50% enzyme activity, which is obtained by measuring a concentration of a substrate which results in 50% inhibition of enzyme activity), $IC_{50}$ values for the individual kinase enzymes are shown in FIG. 4, and a decrease in enzyme activity according to the concentration of compound 1 is plotted in the lower graph shown in FIG. 4. In the graph, the horizontal axis represents a log value for the concentration of compound 1, and the vertical axis represents enzymatic activity.

As a result, the $IC_{50}$ experiment confirmed that compound 1 bound to active sites of the six kinase enzymes to cause a decrease in enzymatic activity, as shown in FIG. 4.

In this case, the $IC_{50}$ values for BRAF and PDGFRa enzymes are not set in the table shown in FIG. 4, but this means that data values does not coincide with a graph equation (Reaction Biology Corp.) in the graph shown in FIG. 4 to calculate an $IC_{50}$ value, but does not mean that there is no inhibitory ability measured. Reference values listed on the right of the table represent $IC_{50}$ values of the kinase inhibitors widely known in the related art, [a] Staurosporine and [b] GW5074.

EXAMPLE 6

Fluorescence Turn-on Imaging by Binding of Compound 1 to Kinase Enzyme

Figure 5:
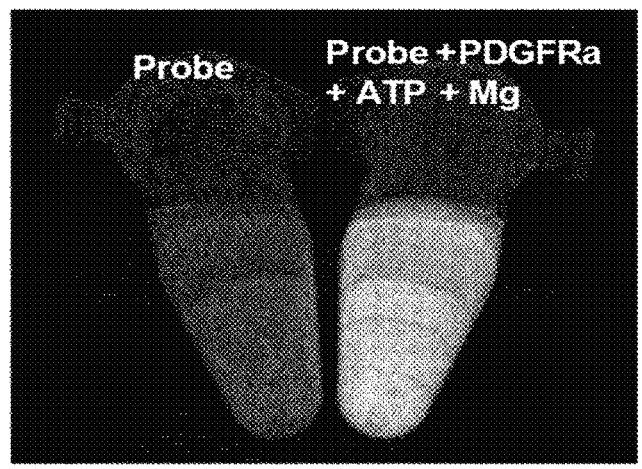
FIG. 5 is an image showing that compound 1 exhibits fluorescence when compound 1 binds to a PDGFRa kinase enzyme.

By using ultraviolet rays (UV), the present inventors confirmed that a fluorescence turn-on response appeared when compound 1 bound to a kinase enzyme. The results are shown in FIG. 5.

More particularly, Model WUV-L10 commercially available from WiseUV was used as a UV excitation device, and the solvent and experiment conditions used were substantially the same as in Example 3. Here, a fluorescence emission observed in the UV excitation device (UV excitation at 350 nm to 430 nm) was determined by taking an image.

As a result, when PDGFRa and the cofactors, ATP and Mg, were added to compound 1, and stirred at 37° C. for 24 hours, compound 1 showed strong fluorescence, compared with when compound 1 was used alone.

EXAMPLE 7

Figure 6:
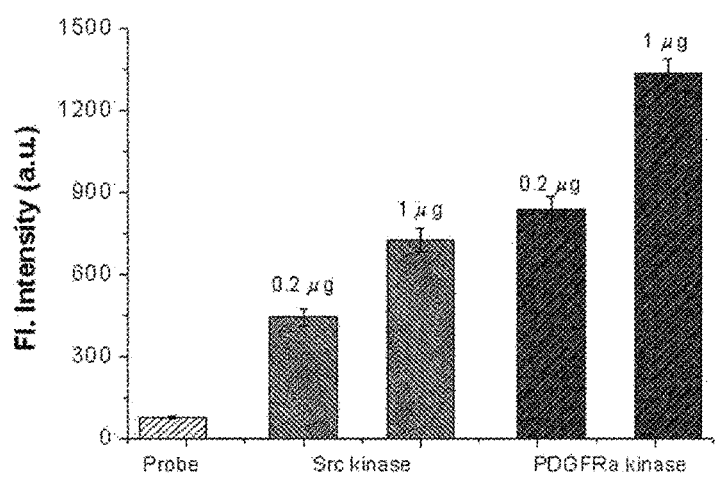
FIG. 6 is a graph illustrating effects of certain kinase enzymes on fluorescence intensities according to concentrations of the kinase enzymes binding to compound 1.

Determination of Effect of Compound 1 on Increase in Fluorescence Intensity According to Concentration of Kinase Enzyme The present inventors determined an effect of compound 1 on an increase in fluorescence intensity according to the concentration of the kinase enzyme. The results are shown in FIG. 6.

More particularly, compound 1 (100 µM) and the kinase enzyme, Src or PDGFRa, were used at contents of 0.2 µg and 1 µg, respectively, and the solvent and experiment conditions used were substantially the same as in Example 3. Then, compound 1 bound to a varying concentration of the kinase enzyme, and an increase in fluorescence signal intensity was observed.

As a result, it was confirmed that compound 1 showed stronger fluorescence signal intensity at higher concentrations of Src and PDGFRa.

EXAMPLE 8

Determination of Effect of Cofactors on Binding of Compound 1 to Kinase Enzymes

The present inventors determined an effect of the cofactor, magnesium (Mg) and adenosine triphosphate (ATP), on binding of compound 1 to the kinase enzymes. The results are shown in FIG. 7.

More particularly, the solvent and experiment conditions used were substantially the same as in Example 3. In the graph shown in FIG. 7, A represents a fluorescence intensity when compound 1 (100 µM) is used alone, B represents a fluorescence intensity when Mg (1 mM) is added to compound 1, C represents a fluorescence intensity when ATP (1 mM) is added to compound 1, and D represents a fluorescence intensity when compound 1 is treated with Mg (1 mM) and ATP (1 mM) at the same time.

Figure 7:
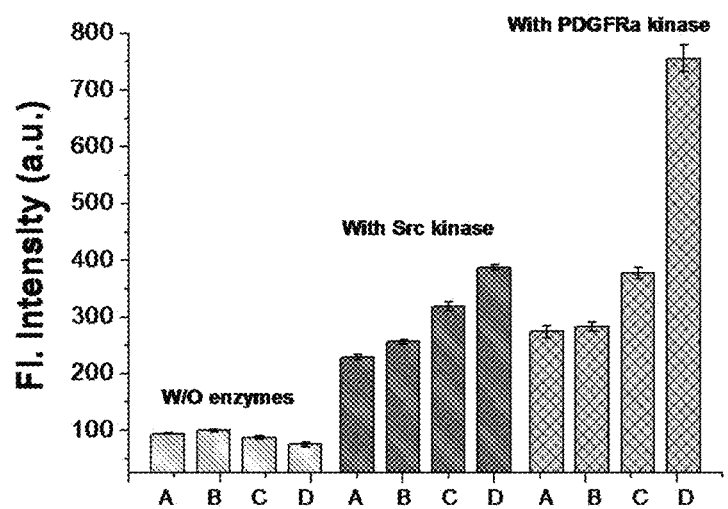
FIG. 7 is a graph illustrating effects of cofactors, magnesium (Mg), and adenosine triphosphate (ATP), on fluorescence intensities upon binding of certain kinase enzymes to compound 1.

As a result, it was revealed that the highest increase in fluorescence intensity was observed for the Src and PDGFRa kinase enzymes in the case of D in which the kinase enzyme was included together with the cofactors, Mg and ATP, as shown in FIG. 7. From these results, it could be seen that the cofactors had great influence on binding of compound 1.

EXAMPLE 9

Binding of Compound 1 to Kinase Enzymes According to Concentration of Compound 1

The present inventors determined a binding level of compound 1 to certain kinase enzymes according to the concentration of compound 1 in the form of fluorescence intensity. The results are shown in FIG. 8.

More particularly, a concentration of the kinase enzyme was set to 0.2 µg/mL, fluorescence intensity according to the concentration of compound 1 was measured in the presence of Mg (1 mM) and ATP (1 mM), and the solvent conditions and other conditions were substantially the same as in Example 3. In this case, the concentrations of compound 1 used in this experiment were 0 µM, 5 µM, 10 µM, 50 µM, 100 µM, and 200 µM, FIG. 10A shows the results for the Src kinase enzyme, and FIG. 10B shows the results for the PDGFRa kinase enzyme.

Figure 8:
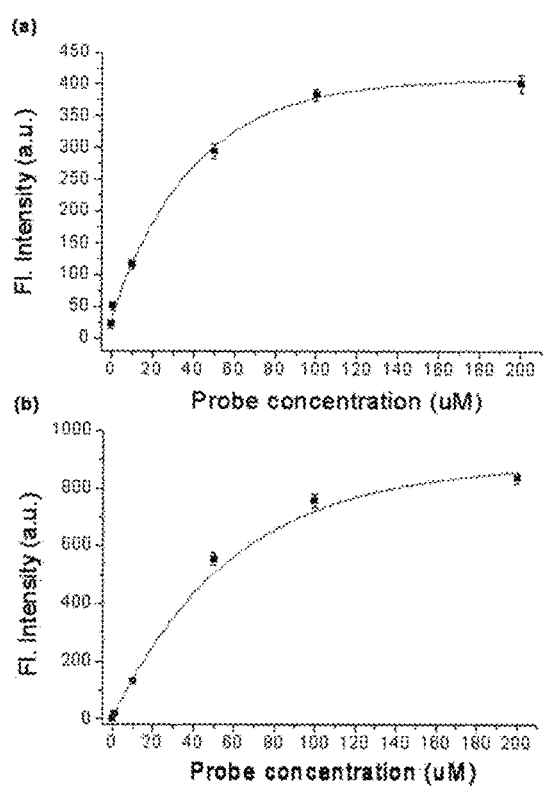
FIG. 8 is a graph illustrating binding levels of compound 1 to certain kinase enzymes according to concentration of compound 1 in the form of fluorescence intensity.

As a result, it was confirmed that each of the two kinase enzymes showed an increase in fluorescence intensity by approximately 50% for compound 1 at a concentration of approximately 50 µM, as shown in FIG. 8. From these results, it could be seen that an increase in fluorescence intensity by 50% or more at the peak when compound 1 was present at a minimum concentration of 50 µM.

EXAMPLE 10

Effect of Inhibitor on Binding of Compound 1 to Kinase Enzyme

The present inventors treated kinase enzymes with a widely known kinase inhibitor together with compound 1, and confirmed an effect of the kinase inhibitor on binding of compound 1 to the kinase enzymes. The results are shown in FIG. 9.

More particularly, an effect of the inhibitor on a total of the six kinase enzymes was determined, and the six kinase enzymes are as follows: (A) ABL, (B) BRAF, (C) PDGFRa, (D) RSK2, (E) Src, and (F) TYK2. This experiment was performed under three different conditions, and the solvent conditions and basic conditions used in this experiment were substantially the same as in Example 3.

Figure 9:
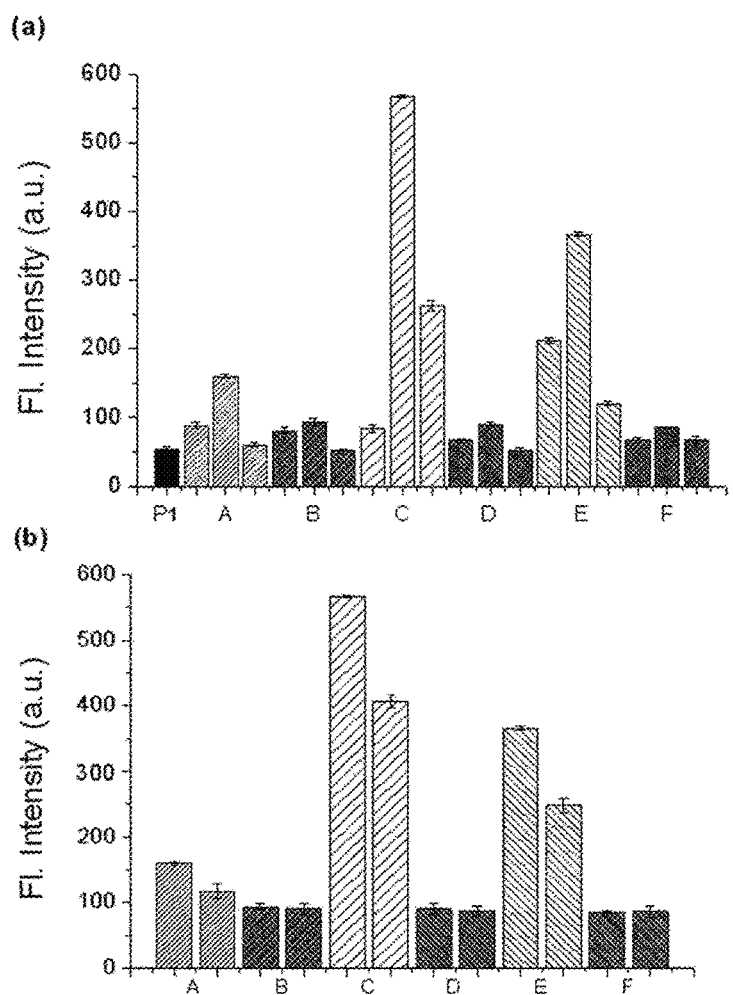
FIG. 9 is a graph illustrating effects of a kinase inhibitor to inhibit binding of compound 1 to kinase enzymes in the form of fluorescence intensity.

In the graph shown in (a) of FIG. 9, the leftmost black bar represents a fluorescence intensity when only compound 1 is present in a solvent, a left bar of each of A to F represents a fluorescence intensity when compound 1 (100 μM) and a kinase enzyme (0.2 μg/ml) are present in a solvent, and middle bar represents a fluorescence intensity when compound 1 (100 μM), a kinase enzyme (0.2 μg/ml), Mg (1 mM), and ATP (1 mM) are included in a solvent, and a right bar represents a fluorescence intensity when an inhibitor (Gleevec, 100 μM) is further included.

As a result, it was confirmed that compound 1 did not selectively bind to the kinase enzymes to cause a sufficient increase in fluorescence intensity when the inhibitor was included, as shown in (a) of FIG. 9.

In the same way, the inhibitor was treated later, and a change in fluorescence intensity was then observed. In the graph shown in (b) of FIG. 9, A to F are substantially the same as those shown in (a) of FIG. 9. In this case, compound 1 (100 μM), ATP (1 mM), Mg (1 mM), and a kinase enzyme (0.2 μg/ml) were stirred for 24 hours (at 37° C.), and an inhibitor (100 μM) was then treated. After treatment of the inhibitor, the resulting mixture was stirred for another 24 hours (at 37° C.). Here, a left bar of each of A to F represents a fluorescence intensity before treatment of the inhibitor, and a right bar of each of A to F represents a fluorescence intensity after treatment of the inhibitor.

As a result, it was revealed that the fluorescence intensity of compound 1 decreased after treatment of the inhibitor, which indicated that the inhibitor bound to the kinase enzyme in competition with compound 1, as shown in (b) of FIG. 9.

Accordingly, it could be seen that compound 1 according to the present invention was used to develop a novel inhibitor inhibiting activities of a kinase enzyme. Here, an inhibitor having strong binding affinity to kinase enzymes binds to the kinase enzymes in competition with compound 1, which results in a decrease in fluorescence intensity. Therefore, compound 1 can be used to provide a standard for easily determining binding affinity of a kinase inhibitor to kinase enzymes.

EXAMPLE 11

Low Cytotoxicity of Compound 1

The present inventors confirmed the cytotoxicity of compound 1 in mouse cutaneous melanoma cells (B16F10) using a cell counting kit-8 (CCK-8) method (Dojindo laboratories, Kumamoto, Japan). The results are shown in FIG. 10.

More particularly, the B16F10 cells were incubated for 24 hours (at 37° C.) at a density of 5000 cells/well in a 96-well plate under a 5% $CO_2$ atmosphere. The cells were treated with an increasing concentration of compound 1 (10 μM, 30 μM, 50 μM, 100 μM, and 200 μM) in a DMSO solvent, and then incubated for an hour. Thereafter, the cells were treated with 10 μL of a CCK-8 solution, and then incubated for 2 hours. Then, the absorbance was observed at a wavelength of 450 nm under a microplate reader (Multiskan EX, Thermo Eletron) to confirm the cytotoxicity of compound 1.

Figure 10:
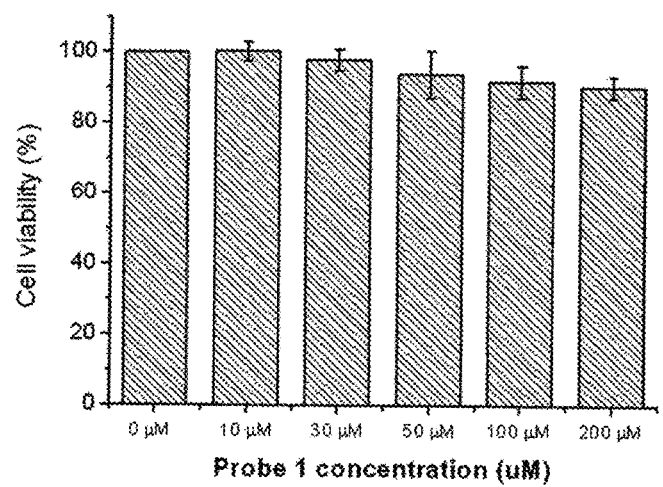
FIG. 10 is a graph showing cytotoxicity of compound 1.

As a result, it was confirmed that compound 1 had more than 90% cell viability at an increasing concentration of 0 to 200 μM, which indicated that compound 1 showed low cytotoxicity, as shown in FIG. 10.

EXAMPLE 12

Fluorescence Turn-on Response after Various Cancer Cells are Treated with Compound 1

The present inventors injected compound 1 into various cancer cells, and determined a fluorescence turn-on response in the cancer cells using single-photon and two-photon fluorescence microscopes. The results are shown in FIG. 11.

More particularly, a total of seven kinds of cancer cells, for example, (a) B16F10 mouse skin cancer cells, (b) CT26 mouse colon cancer cells, (c) SNU-475 human liver cancer cells, (d) A431 human epidermoid carcinoma cells, (e) SKBR3 human breast cancer cells, (f) HeLa human uterine cancer cells, and (g) U87MG human brain tumor cells, were treated with compound 1, and fluorescence images of the cancer cells were observed under a single-photon (confocal) fluorescence microscope (FV1000 model, Olympus) and a two-photon fluorescence microscope (Chameleon Ultra, Coherent, home-built version). Each of the cancer cells were incubated in a minimum essential medium with Earle's balanced salts (MEM/EBSS), a Dulbecco's modified Eagle medium (DMEM), a Roswell Park Memorial Institute (RPMI) medium, a fetal bovine serum (FBS), a penicillin-streptomycin (PS) medium, phosphate buffered saline (PBS), and a trypsin-EDTA culture broth, all of which were commercially available from Hyclone. In this case, the incubation was performed at 37° C. The incubated cells were cultured at 37° C. for 24 hours on a 12 mm glass coverslip so that cells grew to a density of approximately $1 \times 10^5$. Thereafter, the cultured cells were treated with 50 μM of compound 1, and cultured for another one hour, and a culture broth was removed to collect the cells. Subsequently, a 4% formaldehyde solution was added to the cells, and the cells were immobilized on a coverslip. The coverslip was put on a slide glass, and spread using an anti-fading reagent (commercially available from Biomeda). When the preparation was completed, a fluorescence image was obtained using a fluorescence microscope. Then, the single-photon fluorescence microscope image was observed at an excitation wavelength of 405 nm and emission wavelengths of 500 to 550 nm, and the two-photon fluorescence microscope image was observed at an excitation wavelength of 880 nm, emission wavelengths of 500 to 550 nm, and a laser power of 15 mW.

Figure 11:
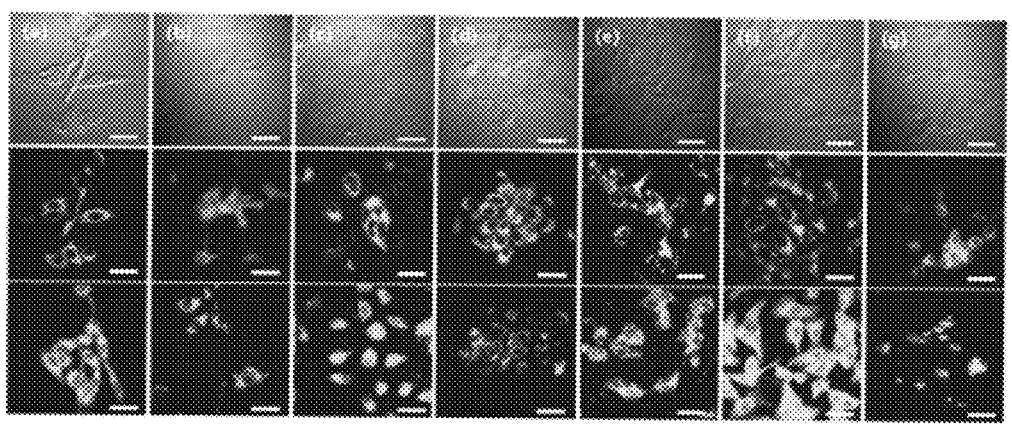
FIG. 11 is an image showing a fluorescence turn-on response after treatment of various cancer cells with compound 1 using single-photon and two-photon fluorescence microscopes.

In FIG. 11, the top panel represents a bright field image, the middle panel represents a single-photon fluorescence microscope image of the cells, and the bottom panel represents a two-photon fluorescence microscope image of the cells. In this case, the images had a width of 170 μm and a height of 170 μm, and a scale bar represents a length of 35 μm.

As shown in FIG. 11, the results observed under the single-photon and two-photon fluorescence microscopes showed that compound 1 provided a bright fluorescence image in the cancer cells. As a result, it could be seen that compound 1 directly bound to the kinase enzyme present in the cancer cells to exhibit fluorescence.

EXAMPLE 13

Emission Wavelengths of Fluorescence in Cancer Cells Treated with Compound 1

The present inventors treated CT-26 cancer cells with compound 1, and determined emission wavelengths of fluorescence using an optical fiber. The results are shown in FIG. 12.

More particularly, CT-26 cancer cells were treated with compound 1 in the same manner as performed in Example 12, and emission wavelengths of fluorescence were then determined using an optical fiber. The optical fiber was connected to a spectrofluorometer (FL1039, HORIBA), and ranges of excitation wavelengths and emission wavelengths are substantially the same as in Example 12. Then, the emission wavelengths of fluorescence were determined.

Figure 12:
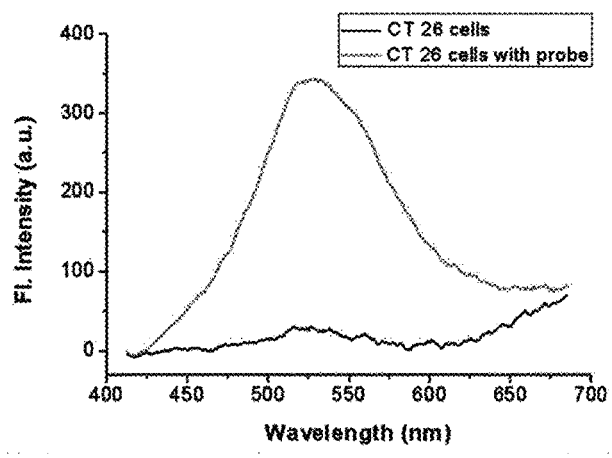
FIG. 12 is a graph illustrating emission wavelengths of fluorescence in CT-26 cancer cells treated with compound 1 using an optical fiber.

As a result, it was revealed that fluorescence was not emitted when the CT-26 cancer cells were not treated with compound 1 (black line), whereas strong fluorescence was emitted around 550 nm when the CT-26 cancer cells were treated with compound 1 (red line), as shown in FIG. 12. From these results, it could be seen that compound 1 bound to the kinase enzyme in the cancer cells to break an intramolecular hydrogen bond.

EXAMPLE 14

Observation of Two-Photon Microscope Images of Skin Cancer Tissues and Normal Tissues Before and after Treatment of Compound 1

The present inventors observed two-photon microscope images of a mouse's ear transplanted with skin cancer tissues before and after the mouse's ear was treated with compound 1. The results are shown in FIGS. 13 and 14.

More particularly, a mouse's ear was transplanted with skin cancer tissues (mouse melanoma skin cancer B16F10), and treated with compound 1 to determine that fluorescence was selectively observed in a site of cancer in living mice under a two-photon microscope. 6-month-old, SPF/VAF immunodeficent female nude mice (BALB/c-nude mice, OrientBio corp.) were used as the mice, and the B16F10 cancer cells were prepared in the same manner as in Example 12. Then, the concentrated cancer cells from which a solution was removed using a centrifuge were injected into one ear of each mouse using a syringe. After 4 day, formation of cancer tissues in the mouse's ear was checked, and 10 μL of compound 1 (10 mM) was injected into the one ear of each mouse. Then, an equivalent amount of compound 1 was also injected into the other ear of each mouse which was not transplanted with the cancer cells (normal tissues including no cancer tissues). After 30 minutes, the mice were anesthetized by breathing 2.5% avertin (which was a respiratory anesthetic), and images were taken of cancer tissues and normal tissues using a two-photon fluorescence microscope. An excitation wavelength was 880 nm, and a laser power was 100 mW.

Figure 13:
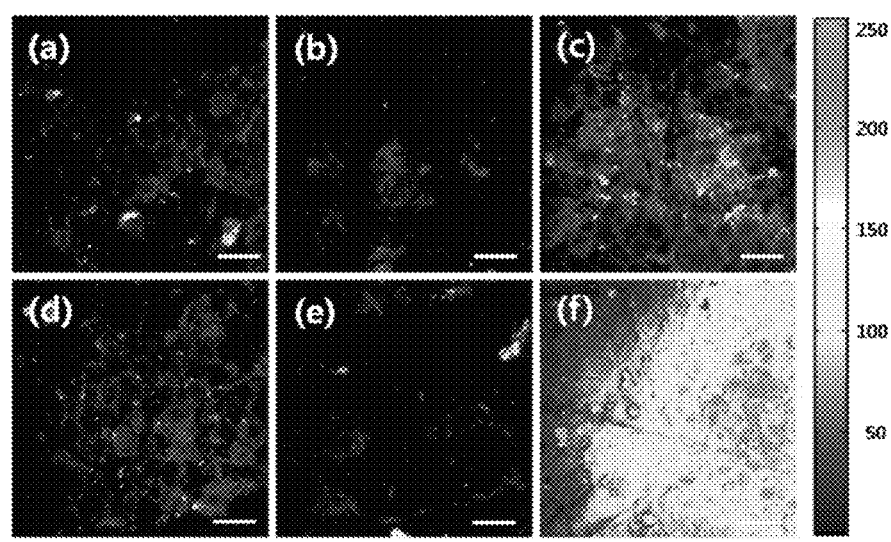
FIG. 13 is an image taken of tissues of skin cancer under a two-photon fluorescence microscope, the tissues of skin cancer being transplanted in a rat after the tissues of skin cancer are treated with compound 1.
Figure 14:
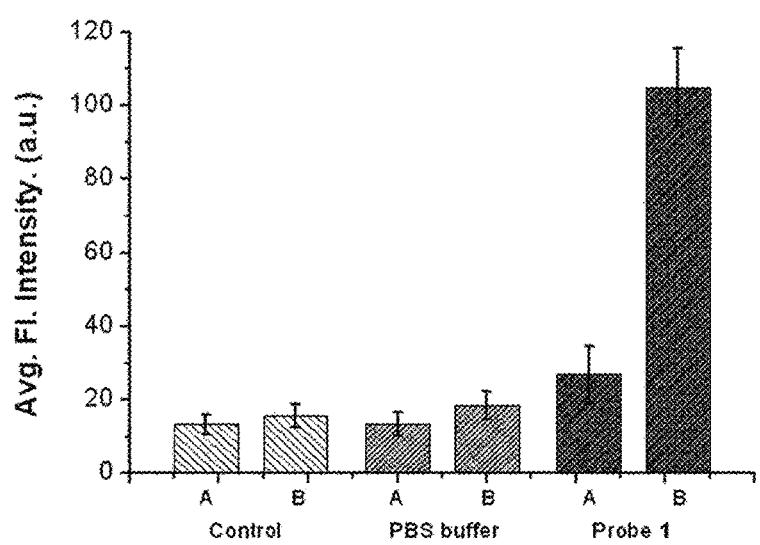
FIG. 14 is a graph illustrating the fluorescence intensities of two-photon fluorescence microscope images shown in FIG. 13.

In FIG. 13, each image has a size of 300 μm×300 μm, and a scale bar represents 50 μm. A right bar represents a fluorescence signal intensity. The upper panels a, b, and c represent images of the normal tissues which are not transplanted with the cancer cells, and the lower panels d, e, and f represent images of the cancer tissues which are transplanted with the cancer cells. The panels a and d show the two-photon fluorescence imaging results from the mice into which nothing is injected, the panels b and e show the two-photon fluorescence imaging results from the mice into which 10 μL of a PBS buffer including no compound 1 is injected, and the panels c and f show the two-photon fluorescence imaging results from the mice into which 100 μL of a solution including compound 1 is injected.

As shown in FIG. 13, it was revealed that a bright fluorescence image was observed in the cancer tissues into which compound 1 was injected. As a result, it could be seen that compound 1 bound to the kinase enzymes in the cancer tissues, and thus strong fluorescence was selectively observed in the cancer tissues as compound 1 stayed in the cancer tissues for an extended period of time.

In this case, FIG. 14 is a graph illustrating the fluorescence intensities of two-photon fluorescence microscope images obtained in FIG. 13. In FIG. 14, A represents normal tissues which are not transplanted with the cancer cells (the upper panels a to c of FIG. 13), B represents cancer tissues which are transplanted with the cancer cells (the lower panels d to f of FIG. 13), and the vertical axis represents a fluorescence intensity.

EXAMPLE 15

Optical Coherence Tomography Results on Skin Cancer Tissues and Normal Tissues Before and after Treatment of Compound 1

The present inventors performed optical coherence tomography on a mouse's ear transplanted with cancer tissues before and after the mouse's ear was treated with compound 1. The results are shown in FIG. 15.

Optical coherence tomography is an effective method of providing information on thicknesses of tissues as images are taken of lateral surfaces of the tissues. In this case, a site in which cancer tissues are formed tends to have a higher thickness than a site in which no cancer tissues are formed.

More particularly, in the present invention, optical coherence tomography (OCT) on a site which were transplanted or a site which were not transplanted with the cancer tissues was performed. OCT was performed simultaneously with two-photon fluorescence microscopy, all the courses for preparing for an experiment were performed in the same manner as in Example 14. OCT used a custom-built wavelength swept source based on a polygonal wavelength filter and a semiconductor optical amplifier (BOA-5785, Covega), a central wavelength was 1310 nm, a width of wavelengths was 105 nm, and a spectral resolution was 0.17 nm. Then, an image having a size of 750 μm×750 μm was obtained.

Figure 15:
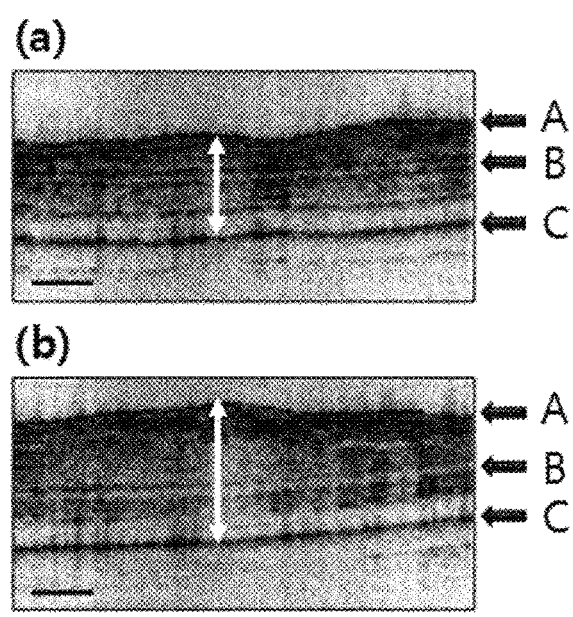
FIG. 15 is an image taken of tissues of skin cancer under an optical coherence tomograph (OCT) before and after the tissues of skin cancer are treated with compound 1.

In FIG. 15, A represents an upper epidermis of the mouse's ear, B represents a cartilage, C represents a lower epidermis of the mouse's ear, and a scale bar represents 100 μm.

As shown in FIG. 15, it was confirmed that the sample in which the cancer was not present had a thickness of approximately 180 μm as shown in (a) of FIG. 15, whereas the sample in which the cancer was present had a thickness of approximately 250 μm as shown in (b) of FIG. 15, which indicated that the cancer tissues were formed with a higher thickness than the normal tissues.

In addition, the OCT results showed that a background image whose data was able to be combined with a two-photon fluorescence microscope image obtained in Example 14 was provided.

EXAMPLE 16

3D Imaging Results for Skin Cancer Tissues and Normal Tissues Before and after Treatment of Compound 1

The present inventors performed two-photon microscopy and optical coherence tomography on a mouse's ear transplanted with cancer tissues before and after the mouse's ear was treated with compound 1, and the two resulting images were combined. The results are shown in FIG. 16.

Figure 16:
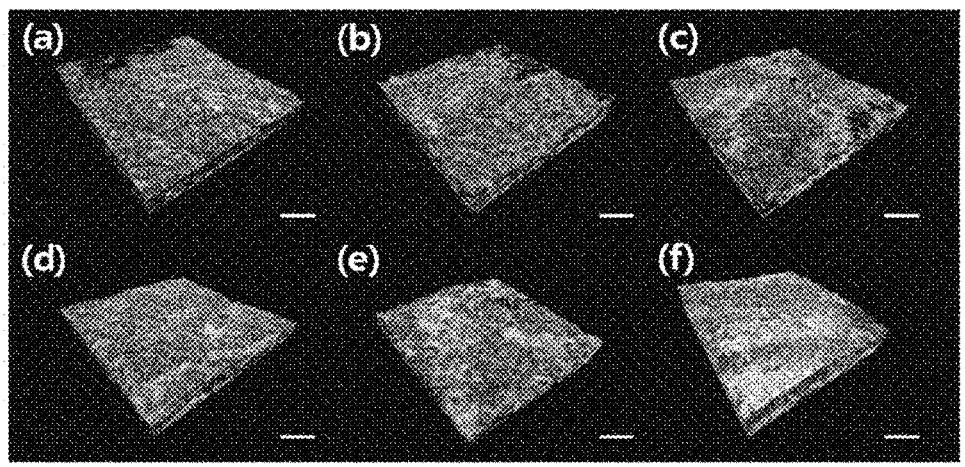
FIG. 16 is a 3D image taken of tissues of skin cancer and normal tissues under a two-photon fluorescence microscope and an optical coherence tomograph at the same time after the tissues of skin cancer and the normal tissues are treated with compound 1.

More particularly, (a) to (f) of FIG. 16 are images obtained under the same experiment conditions as in Example 14, and 3D images are obtained by overlapping two-photon fluorescence microscopy images and optical coherence tomography images, as described above in Examples 14 and 15. In this case, a scale bar represents 50 μm.

From the 3D imaging results, it could also be seen that fluorescence was strongly emitted from the wide tissues when the cancer tissues were treated with compound 1, as shown in FIG. 16.

The fluorescent probe of the present invention has two-photon excitation characteristics. That is, the fluorescent probe has advantages in that it can be less affected by high cell permeability, low cell injury, and extinction by in vivo hemoglobin due to the excitation characteristics of the single-photon fluorescent probe which is excited using energy of wavelengths corresponding to the half of the wavelengths (or twice the wavelengths) of the fluorescent probe, and may offer very high resolution since only a focal site is excited.

Also, since the fluorescent probe of the present invention is a small organic molecule which can emit a fluorescence signal when the small organic molecule binds to a tyrosine kinase, the fluorescent probe can be applied to solve the problems of a conventional fluorescent probe having a complicated structure to detect a kinase enzyme. Also, when a kinase enzyme associated with signal transduction is overexpressed in cells such as cancer cells, compared to normal cells, much more intense fluorescence is observed in the cancer cells than the normal cells. Accordingly, the fluorescent probe of the present invention can be effectively used to selectively image the cancer cells or tissues in the normal cells or tissues.

In addition, the binding affinity is evaluated through competitive binding between the fluorescent probe and a drug inhibiting a kinase enzyme to develop the drug. As a result, the fluorescent probe of the present invention can be effectively used to screen a drug inhibiting overexpression of the kinase enzyme.

It will be apparent to those skilled in the art that various modifications can be made to the above-described embodiments of the present invention without departing from the scope of the invention. Thus, it is intended that the present invention covers all such modifications provided they come within the scope of the appended claims and their equivalents.

What is claimed is:

1. A method of detecting a tyrosine kinase in a biological sample, the method comprising:
    a) contacting the biological sample with an effective amount of a compound represented by the following Formula 1

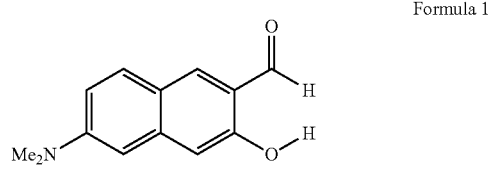 [SMILES: CN(C)c1ccc2cc(C=O)c(O)cc2c1]

Formula 1 b) measuring fluorescence from the sample that the compound has contacted; and
   c) at least based on measured fluorescence relative to one or more controls, determining either or both of the existence and a level of a tyrosine kinase in the sample.

2. The method of claim 1, wherein the compound comprises an intramolecular hydrogen bond in an ortho-hydroxy-benzaldehyde structure thereof, wherein the compound exhibits changes in fluorescence when the intramolecular hydrogen bond breaks as the compound and the tyrosine kinase bind with each other.

3. The method of claim 1, wherein the tyrosine kinase is selected from the group consisting of ABL1 (T315I), BRAF, PDGFRa, RSK2, TYK2, and Src.

4. The method of claim 1, wherein measuring the fluorescence is performed using at least one apparatus selected from the group consisting of a confocal fluorescence microscope, a two-photon fluorescence microscope, and an optical coherence tomograph.

5. The method of claim 1, wherein the biological sample comprises cancer cells and tissues.

6. The method of claim 1, wherein the biological sample is a biopsy sample comprising cells and/or tissues from a subject, and wherein the cells and/or tissues of the biological sample are contacted with the compound of Formula 1 in vivo by administering the compound to a subject.

* * * * *